(12) United States Patent
Hille et al.

(10) Patent No.: US 9,616,045 B2
(45) Date of Patent: Apr. 11, 2017

(54) TRANSDERMAL THERAPEUTIC SYSTEM HAVING IMPROVED LONG-TERM WEARING COMFORT

(71) Applicant: LTS Lohmann Therapie-Systeme AG, Andernach (DE)

(72) Inventors: Thomas Hille, Neuwied (DE); Lothar Deurer, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 14/506,105

(22) Filed: Oct. 3, 2014

(65) Prior Publication Data
US 2015/0024028 A1 Jan. 22, 2015

Related U.S. Application Data

(62) Division of application No. 13/405,689, filed on Feb. 27, 2012, now Pat. No. 8,883,198, which is a division
(Continued)

(30) Foreign Application Priority Data

Dec. 5, 2001 (DE) .................................. 10 159 745

(51) Int. Cl.
*A61K 9/70* (2006.01)
*A61K 31/381* (2006.01)
(Continued)

(52) U.S. Cl.
CPC .......... *A61K 31/381* (2013.01); *A61K 9/0014* (2013.01); *A61K 9/7023* (2013.01);
(Continued)

(58) Field of Classification Search
CPC .. A61K 9/7084; A61K 9/0014; A61K 9/7053; A61K 9/7061; A61K 9/7023
See application file for complete search history.

(56) References Cited

U.S. PATENT DOCUMENTS 3,953,566 A 4/1976 Gore
4,810,499 A 3/1989 Nuwayser
(Continued)

FOREIGN PATENT DOCUMENTS

AU 199895329 B2 8/1998
CA 2326630 A1 10/1999
(Continued)

OTHER PUBLICATIONS

PubChem, Rotigotine, U.S. National Library of Medicine National Center for Biotechnology Information, http://pubchem.ncbi.nlm.nih.gov/compound/59227, p. 1-20, entry created Aug. 8, 2005 (last accessed Sep. 4, 2015).
(Continued)

*Primary Examiner* — Carlos Azpuru
(74) *Attorney, Agent, or Firm* — Frommer Lawrence & Haug LLP

(57) ABSTRACT

The invention relates to transdermal therapeutic systems (TTS) comprising a backing, a reservoir layer containing at least one pharmaceutical active ingredient, and an adhesive. Said transdermal therapeutic systems are characterised in that they are able to continuously adhere to the surface of the skin over a long period of time. During said long period of time, a) there is at least one time interval during which the TTS adhering to the surface of the skin is intensively exposed to water, and b) the active ingredient is transdermally released. The invention also relates to a method for the continuous transdermal release of at least one pharmaceutical active ingredient over a long period of time.

32 Claims, 1 Drawing Sheet

Related U.S. Application Data of application No. 12/858,720, filed on Aug. 18, 2010, now Pat. No. 8,628,795, which is a division of application No. 10/497,577, filed as application No. PCT/EP02/12875 on Nov. 16, 2002, now Pat. No. 7,824,707.

(51) Int. Cl.
  A61K 9/00     (2006.01)
  A61K 31/485   (2006.01)

(52) U.S. Cl.
  CPC .......... *A61K 9/7038* (2013.01); *A61K 9/7053* (2013.01); *A61K 9/7061* (2013.01); *A61K 9/7069* (2013.01); *A61K 9/7084* (2013.01); *A61K 31/485* (2013.01)

(56) References Cited

U.S. PATENT DOCUMENTS

| | | | |
|---|---|---|---|
| 4,820,525 | A | 4/1989 | Leonard et al. |
| 4,824,676 | A | 4/1989 | Bodor |
| 4,911,916 | A | 3/1990 | Cleary |
| 5,089,267 | A | 2/1992 | Hille et al. |
| 5,230,898 | A | 7/1993 | Horstmann et al. |
| 5,246,705 | A | 9/1993 | Venkatraman et al. |
| 6,814,976 | B1 | 11/2004 | Hille et al. |
| 7,175,853 | B1 | 2/2007 | Bracht |
| 7,824,707 | B2 | 11/2010 | Hille et al. |
| 2003/0133970 | A1 | 7/2003 | Bracht et al. |
| 2004/0071764 | A1 | 4/2004 | Bracht |
| 2004/0265363 | A1 | 12/2004 | Hille et al. |

FOREIGN PATENT DOCUMENTS

| | | |
|---|---|---|
| CA | 2326662 A1 | 10/1999 |
| CA | 2372339 A1 | 11/2000 |
| DE | 235923 A1 | 5/1986 |
| DE | 3843239 C1 | 2/1990 |
| DE | 3910543 A1 | 10/1990 |
| DE | 19738855 A1 | 3/1999 |
| DE | 19814087 A1 | 10/1999 |
| DE | 19923551 A1 | 11/2000 |
| DE | 10027258 C1 | 10/2001 |
| DE | 10049225 A1 | 4/2002 |
| DE | 10103860 A1 | 8/2002 |
| DE | 10159745 A1 | 7/2003 |
| EP | 247863 A2 | 12/1987 |
| EP | 274863 A2 | 7/1988 |
| EP | 427877 A1 | 5/1991 |
| WO | WO-90-06736 A1 | 6/1990 |
| WO | WO-9949852 | 10/1999 |
| WO | WO-03-047556 | 6/2003 |

OTHER PUBLICATIONS

J. Thomas Hutton et al., *Transdermal Dopminergic $D_2$ Receptor Agonist Therapy in Parkinson's Disease With N-0923 TDS: A Double-Blind, Placebo-Controlled Study*, Movement Disorders, vol. 16., No. 3, pp. 459-463 (May 9, 2001).

Leo Verhagen Metman et al., *Continuous Transdermal Dopaminergic Stimulation in Advanced Parkinson's Disease*, 24(3) Clinical Neuropharmacology 163-169 (May/Jun. 2001).

Denise Lowe Walters et al., *Development and Validation of a Gradient Reversed-Phase High-Performance Liquid Chromatographic Assay for S(−)-2-(N-propyl-N-2-thienylethylamino)-5-hydroxytetralin (N-0923) from a Transdermal Delivery System*; 670 Journal of Chromatogrphy B. 299-307 (1995).

Izaak den Daas et al., *Transdermal Administration of the Dopamine Agonist N-0437 and Seven Ester Prodrugs: Comparison with Oral Administration in the 6-OHDA Turning Model*, 342 Naunyn-Schmiedeberg's Archives of Pharmacology 655-659 (1990).

Wia Timmerman et al., *Microdialysis and Striatal Dopamine Release: Stereoselective Actions of The Enantiomers of N-0437*; 162 European Journal of Pharmacology 143-150 (1989).

Peter A. Loschmann et al., *Steroselective Reversal of MPTP-Induced Parkinsonism in the Marmoset After Demal Application of N-0437*; 166 European Journal of Pharmacology 373-380 (1989).

Alain Munoz; OESCLIM: An Advanced Delivery System for HRT; Munoz/Maturitas 33, 1999, pp. S39-S47, also referred to as XP-002230986.

"Corona Pretreatment to obtain wettability and adhesion", Softal Electronic Report, Nr. 102 E, Softal Electronic GmbH, Hamburg.

Letter from Oxyphen AG to Novosis AG dated Jan. 31, 2001 with brochure for RoTrac® Capillary Pore Membranes.

"Oberflächentechnik", http://www.fh-muenster.de/fb3/studierende/index_new.php?p=3#a1.

Physik—Ein Lehrbuch zum Gebrauch neben Vorlesungen (Physics—Teacher's Edition to Accompany Lectures), ed. Dr. Helmut Volgel, Publ. Springer-Verlag Berlin, pp. 109-112 (1974).

Rozenbaum et al; Comparison of Two Estradiol Transdermal Systems (Oesclim 50 and Estraderm TTS 50). Tolerability, Adhesion and Efficacy; H. Rozenbaum et al/Maturitas 25, 1996, pp. 161-173; also referred to as XP-002230890.

Taurelle et al; The Long Term Tolerability and Efficacy of OESCLIM: Results of a 1-Year Study; Taurelle et al/Maturitas 33, 1999, pp. S73-S81; also referred to as XP-002230989.

TRANSDERMAL THERAPEUTIC SYSTEM HAVING IMPROVED LONG-TERM WEARING COMFORT

The present application is a divisional of U.S. patent application Ser. No. 13/405,689 filed on Feb. 27, 2012, which is a divisional of U.S. patent application Ser. No. 12/858,720 filed on Aug. 18, 2010, now U.S. Pat. No. 8,628,795, which is a divisional of U.S. patent application Ser. No. 10/497,577 filed on Jun. 3, 2004, now U.S. Pat. No. 7,824,707, which claims priority from PCT Patent Application No. PCT/EP02/12875 filed on Nov. 16, 2002, which claims priority from German Patent Application No. DE 10 159 745.2 filed on Dec. 5, 2001.

The invention relates to a transdermal therapeutic system (TTS) for the controlled administration of an active pharmaceutical ingredient. The TTS is suitable for prolonged, in particular several days', administration of the active ingredient and makes continuous contact possible with the surface of a user's skin even during a time segment characterized by intensive exposure to water of the TTS applied to the surface of the skin, without unwanted detachment occurring.

Transdermal therapeutic systems (TTS), are patches having a layered structure and comprising at least one active pharmaceutical ingredient in a reservoir layer. A distinction is made between matrix-type and reservoir-type TTS: in the first case the reservoir layer containing the active pharmaceutical ingredient has a pressure-sensitive adhesive finish, and in the second case a membrane which controls the rate of release of the active pharmaceutical ingredient, and where appropriate an additional pressure-sensitive adhesive layer, are present.

Most commercially available TTS are designed for 24-hourly use. However, there are also so-called three-day patches which are intended to be worn by the user (e.g. a person requiring continuous administration of the active pharmaceutical ingredient over a prolonged period, patient, etc.) over a period of at least 72 hours, e.g. Duragesic. The intended period of use is a typical characteristic for a specific transdermal therapeutic system and is evident in each case from the instructions for use in the package insert.

The ability of a TTS to function is based on the concentration of the active pharmaceutical ingredient in the reservoir layer being distinctly higher than in the blood vessels located underneath the surface of the user's skin onto which the transdermal therapeutic system is applied (site of application). This concentration gradient results in a directed diffusion which, after a short initial period (the so-called lag time), ensures a substantially constant active ingredient flux.

In this case there is formation of a dynamic equilibrium between the active ingredient-containing reservoir layer of the TTS, the membrane which is present where appropriate, the pressure-sensitive adhesive layer which is present where appropriate, the layers of skin located below the surface of the user's skin onto which the TTS is applied, and the blood circulation. Interruption of this dynamic equilibrium—for example by a brief removal of the TTS, may lead to the conditions of the dynamic equilibrium set up after the initial period being considerably altered, and it not being possible to ensure continuous and constant administration of the active pharmaceutical ingredient.

Problems may also arise during long-term application of TTS through a patient developing a pronounced sensation of a foreign body because of the rigidity of this system, especially the backing layer. In addition, this rigidity of one component (active ingredient-containing matrix, backing layer etc.) may result in the TTS becoming detached or even falling off the skin, because not only good adhesive properties, but also sufficient flexibility of the TTS is necessary for adequate adhesion of the TTS, because a TTS should adapt to the movements of the skin.

In addition, the wearing of a TTS almost always—especially on wearing for more than 24 hours—leads to occlusion of the site of application, because the skin at this site is able to secrete sweat to only a limited extent. This leads on the one hand to hydration of the skin, and on the other hand the growth of microorganisms is favored in the moist and warm microclimate.

The loss of active ingredient in the reservoir layer occurring through the administration of the active pharmaceutical ingredient may also alter considerably the composition of this layer. This may be of importance when the active pharmaceutical ingredient can act as plasticizer for the polymeric material of which the reservoir layer is composed. Such effects may be compensated where appropriate by adding other plasticizers and/or changing the degree of polymerization and/or crosslinking of the polymeric material used in the composition of the reservoir layer.

Another problem which may occur on use of a TTS over a prolonged period (at least 24 hours) is that relatively large amounts of moisture reach the TTS and bring about decomposition of the constituents of the reservoir layer and/or an unwanted detachment from the surface of the skin.

Moisture of concern in this connection is, on the one hand, perspired water—water secreted by the sweat glands located underneath the site of application of the TTS on the user's skin—and water which may reach the outside of the TTS applied to the surface of the user's skin for example during washing (bathing, showering, sauna etc.).

The TTS is exposed to the perspired water throughout the period of use, the total amount representing a relatively small but continuously existing stress for the TTS. During bathing, showering etc., by contrast, the TTS is exposed to water which approaches from the outside for a particular time segment, but with considerably greater intensity.

U.S. Pat. No. 4,911,916 discloses a transdermal therapeutic system (TTS) having an elastic backing layer, a diffusion matrix composed of a reticulate, macroporous polymer film and a hydrophobic pressure-sensitive adhesive layer. The pores of the macroporous diffusion matrix contain a viscoelastic polymer which comprises an at least partially dissolved active ingredient. The backing layer is chosen so that it ensures the occlusivity of the TTS. The advantage achieved thereby is an increase in the rate of permeation of the active ingredient.

SUMMARY OF THE INVENTION

It is an object of the invention to administer an active pharmaceutical ingredient over a prolonged period to a person requiring a controlled and continuous administration of this active ingredient over a prolonged period.

A further object is to provide a transdermal therapeutic system (TTS) which makes continuous wearing of this TTS possible on a particular site on the surface of the skin (application site) over a prolonged period and ensures during this period a controlled and continuous administration of this active ingredient.

A further object is to prevent unwanted detachment of this TTS during the prolonged period, even if within this period there is at least one time segment in which the transdermal therapeutic system is exposed to intensive contact with water.

A further object is to provide an adhesive matrix for a transdermal therapeutic system (TTS) which makes it possible for this TTS to be worn continuously over a prolonged period, in particular under conditions such that within this period there is at least one time segment in which the transdermal therapeutic system is exposed to intensive contact with water.

A further object is to provide a TTS design which makes it possible for perspired water (perspiration, evaporation of sweat) to diffuse out through the various layers of the TTS.

The object is achieved by a method in which a transdermal therapeutic system (TTS) which has a reservoir layer comprising at least one active pharmaceutical ingredient is applied over a prolonged period to the surface of a user's skin, adheres there (at the specific site of application) continuously, and delivers the active pharmaceutical ingredient transdermally. The transdermal therapeutic system used in this case is likewise part of the achievement of the object.

The prolonged period includes the time between the attachment of a transdermal therapeutic system to the surface of a user's skin and the removal of this transdermal therapeutic system after the intended period of use has elapsed. The prolonged period is a period of at least 24 hours, preferably of at least 48 hours and particularly preferably a period of at least 72 hours. In a further particularly preferred embodiment, the prolonged period comprises at least about 168 hours. It will be appreciated that the skin gives off perspired water (sweat) during the prolonged period. The prolonged period corresponds to the period of use of a single specific TTS.

The intended period of use is a particular characteristic of a transdermal therapeutic system and is normally to be found from the package insert. Within the period of use, the delivery of active ingredient by the TTS is substantially constant. The prolonged period may include at least one time segment of intensive exposure to water of the TTS adhering to the surface of the skin.

A time segment of intensive exposure to water of the TTS adhering to the surface of the skin means, for example, the case of a bath, of a shower or of a visit to a sauna. Such a time segment naturally depends on the individual user, but in certain cultural circles the duration and extent of body cleaning involves a prolonged time of contact with water. Such time segments may normally last from a minimum of 1 minute to a maximum of 30 minutes, with an average duration of from 5 to 15 minutes being assumed.

DETAILED DESCRIPTION OF EMBODIMENTS

Figure 1:
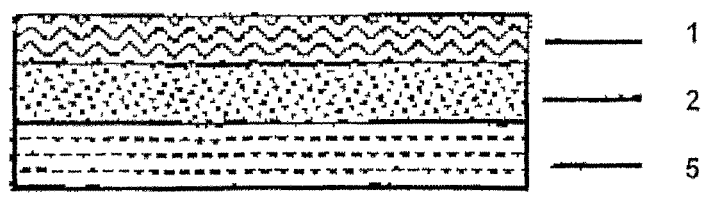
FIG. 1 depicts a transdermal therapeutic system with a backing layer, a reservoir layer and a support film, but without a control membrane.
Figure 2:
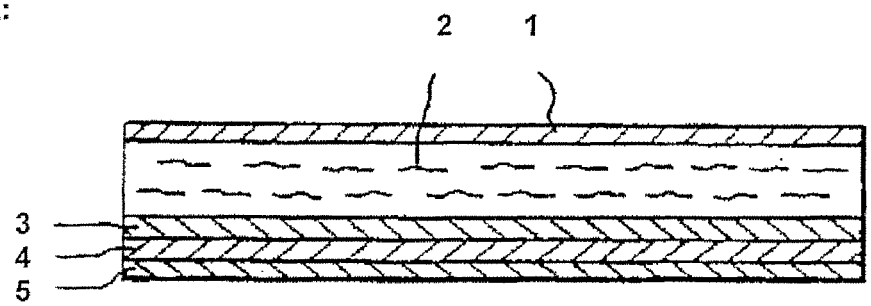
FIG. 2 depicts a transdermal therapeutic system with a backing layer, a reservoir layer, a control membrane, a pressure-sensitive adhesive layer and a support film.
Figure 3:
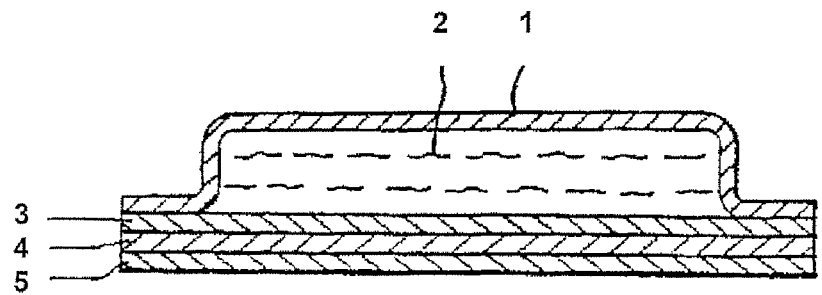
FIG. 3 depicts a transdermal therapeutic system with a backing layer, a reservoir layer, a control membrane, a pressure-sensitive adhesive layer and a support film, and wherein a part of the backing layer contacts the control membrane.

The term continuous for the purpose of this description means that the contact between the surface of the user's skin onto which the TTS has been applied (i.e. the site of application) and the side of the transdermal therapeutic system from which the at least one active pharmaceutical ingredient is delivered to the surface of the user's skin is not interrupted throughout the prolonged period. This means that no unwanted detachment from the surface of the skin takes place during the period between the attachment of a transdermal therapeutic system to the specific site of application on the surface of a user's skin and the removal of this transdermal therapeutic system after the intended period of use has elapsed.

The term continuous in connection with the adhesion to the surface of the skin is not to be strictly equated with a continuous administration of the active pharmaceutical ingredient to the user, because normally—as described above—first a dynamic equilibrium must be generated between the active ingredient-containing reservoir layer, the layers of skin and the blood vessels of the user. These diffusion-related manifestations have the effect that, during a so-called lag time, no or only a small amount of the at least one active pharmaceutical ingredient is delivered to the skin. This lag time is, however, in general negligibly short in relation to the complete time between the application to the surface of the skin and the removal of the transdermal therapeutic system, i.e. the intended application period. The lag time is moreover important only on initial use of a TTS, because normally a transdermal therapy involves a plurality of TTS being applied in chronological sequence.

The term transdermal means the percutaneous delivery of at least one active pharmaceutical ingredient to a user (patient), with at least one active pharmaceutical ingredient being delivered from a transdermal therapeutic system to the surface of the user's skin and migrating through the various layers of skin (e.g. stratum corneum, dermis, cutis and subcutis) located underneath the site of application of the TTS until it is taken up by the underlying blood vessels.

The transdermal therapeutic system (TTS) of the invention which can be employed within the framework of said method includes a backing layer, a reservoir layer comprising the at least one active pharmaceutical ingredient, and an adhesive. During storage, such a TTS is normally located on a redetachable protective layer from which it is removed immediately before application to the surface of the user's skin. A TTS protected in this way is stored in the blister pack or a side-sealed bag.

The backing layer is located on the TTS side facing away from the backing. It may be in the form of a film web, of a fabric or of a combination of these two embodiments. The backing layer is preferably flexible, by which is meant the ability to bend easily when exposed to a small force directed perpendicularly onto the layer.

A film web means a sheet-like material which is preferably flexible. The thickness of such a film web can be between 2 and 50 µm, preferably between 5 and 36 µm and particularly preferably between 9 and 23 µm. The film web may consist of plastic or metal or comprise at least one of these materials in a composite laminate. The film web may be transparent or opaque.

Any synthetically preparable polymeric material is in principle suitable as a plastic of which the backing layer can consist, although polyester, preferably polyethylene terephthalate, is preferred. However, polyurethanes and polyether/ester elastomers (block polymers of partially crystalline polybutylene terephthalate and polyether diols or long-chain aliphatic dicarboxylic esters) are also particularly suitable therefor. A particularly suitable metal is aluminum.

Film webs which can be employed as composite laminate are those obtained by gluing, laminating, cladding or extruding from at least one first plastic and a further plastic or metal. In a particular embodiment, the film web can be perforated, and the pores may have a diameter between 2 μm and 150 μm. The pore density can be between 200 to 2500 pores per cm², preferably between 500 and 1700. A preferred pore shape has a funnel-shaped orifice structure, resulting in specific capillary properties. While the "smooth" side of such a film web ensures a free passage for water, the rough side acts as barrier. A perforated film web with funnel-shaped orifice structure as backing layer is therefore disposed in the TTS in such a way that its rough side points toward the side facing away from the skin.

A fabric means a woven product which is normally produced from warp threads and weft threads. The filamentary starting material of a fabric can consist of natural or synthetic polymeric materials. A suitable natural polymeric material may be, for example, cellulose, silk and cotton, and a suitable synthetic polymeric material may be, for example, polyvinyl chloride, polyurethane, polyester, polyamide, Nomex, Kevlar, polypropylene, polyacryl, Preox, Trevira, nylon or viscose rayon.

The backing layer may be impermeable to active ingredient, by which is meant that the backing layer is able to prevent the active pharmaceutical ingredient passing out through the backing layer. The backing layer may be permeable to moisture, by which is meant that the backing layer is permeable to water vapor and/or water in liquid form. In a preferred embodiment, however, the backing layer is impermeable to water in liquid form.

The backing layer may also be elastic, which is very important for wearing comfort. By this is meant that, when an external tensile force is applied, the backing layer is capable of stretching and, when the tensile force is removed, this is likewise canceled. The backing layer then returns to the original dimensions. This reversible change in dimensions is possible in at least one direction and amounts to at least 10%, preferably at least 30%. In a particularly preferred embodiment, the backing layer is elastic and permeable to water vapor.

The reservoir layer contains the at least one active pharmaceutical ingredient and at least one polymeric carrier material. The content of the at least one active pharmaceutical ingredient in the reservoir layer is between 0.5 and 45% by weight, preferably between 3 and 25% by weight. The content of the at least one active pharmaceutical ingredient in the reservoir layer is sufficient for the active ingredient to be delivered continuously to the surface of the skin during the prolonged period. The content of the at least one active pharmaceutical ingredient is additionally sufficient for the adhesion of the TTS not to be interrupted by the at least one time segment of intensive exposure to water (within the prolonged period) of the TTS adhering to the surface of the skin, i.e. no detachment of the TTS takes place.

Suitable as active pharmaceutical ingredient are slimming agents, appetite suppressants, therapeutic agents for acidosis, Alzheimer's drugs, analeptics, antihypoxemics, analgesics, antirheumatics, anthelmintics, antiallergics, antianemics, antiarrhythmics, antibiotics, antiinfectives, antidementia drugs (nootropics), antidiabetics, antidotes, antieetics, antivertigo drugs, antieplipetics, antihemorrhagics (antifibrinolytics), antihypertensives, antihypoglycemics, antihypotensives, anticoagulants, antimycotics, antiparasitic drugs, anti-inflammatory drugs, antitussives, expectorants, arteriosclerosis drugs, balneotherapeutic agents and agents for thermotherapy, beta-receptor blockers, calcium channel blockers, inhibitors of the renin-angiotensin system, bronchodilators, antiasthmatics, cholagogues, biliary therapeutic agents, cholinergics, corticoids, dermatologicals, disinfectants, antiseptics, dietetic agents, alimentary therapeutic agents, diuretics, blood flow-stimulating agents, anticraving drugs, enzyme inhibitors, enzyme preparations, transport proteins, fibrinolytics, geriatric drugs, antigout drugs, drugs for influenzal infections and colds (influenza remedies), gynecologicals, hemorrhoid remedies (proctologicals), hepatic drugs, hypnotics, sedatives, pituitary hormones, hypothalamus hormones, regulatory peptides and their inhibitors, immunotherapeutic agents, cytokines, cardiac drugs, caries remedies, periodontosis remedies, coronary drugs, laxatives, lipid-lowering agents, local anesthetics, neurotherapeutic agents, gastrointestinal drugs, migraine remedies, minerals, muscle relaxants, anesthetics, parathyroid hormones, calcium metabolism regulators, osteoporosis remedies, neuropathy products, neurotropic agents, ophthalmologicals, otologicals, anti-parkinson drugs, drugs for extrapyramidal disorders, psychoactive drugs, rhinologicals, sinusitis remedies, roborants, tonics, thyroid therapeutic agents, sera, immunoglobulins and vaccines, sex hormones and their inhibitors, spasmolytics, platelet aggregation inhibitors, anti-tuberculosis drugs, stimulants, urologicals, vein therapeutic agents, vitamins, wound-treatment agents, cytostatics and metastasis inhibitors.

These include inter alia in particular: 17β-estradiol, norethisterone, physostigmine, norelgestromin, norethisterone acetate, nitroglycerin, nicotine, clonidine, moxonidine, fentanyl, testosterone, buprenorphine, galanthamine, rivastigmine, morpine, diamorphine, buprion, sildenafil, (−)-5,6,7,8,-tetrahydro-6-[propyl[2-(2-thienyl)ethyl]amino]-1-naphthol, methylphenidate, ethinylestradiol and (S)—N-ethyl-3-[1-dimethylamino)ethyl]-N-methyl-phenyl-carbamate.

The at least one active pharmaceutical ingredient is present in the reservoir layer of the TTS in an amount sufficient for the at least one active pharmaceutical ingredient to be delivered in an effective amount to the blood circulation over the intended prolonged period (period of use). By this is meant that, where appropriate, an initial phase may occur, during which the delivery of active ingredient does not correspond to the substantially constant delivery of active ingredient during the predominant part of the prolonged period (lag time).

The polymeric carrier material forms an essential constituent of the reservoir layer. Suitable possibilities are: water-repelling polymers, water-swellable polymers, water-soluble polymers, water vapor-permeable polymers, which are known to a skilled worker.

The underside of this reservoir layer may be identical to the side of the transdermal therapeutic system for which the active pharmaceutical ingredient is delivered to the surface of the user's skin ("skin side"=the side of the TTS releasing the active ingredient). However, if a membrane controlling the rate of release of the active ingredient and/or an additional pressure-sensitive adhesive layer are present and disposed underneath the reservoir layer, these accordingly form this side of the TTS.

One component of the reservoir layer which confers pressure-sensitive adhesive properties thereon is possibly an adhesive. The adhesive may also be a separate pressure-sensitive adhesive layer which is applied to the side of the TTS facing the skin, or a cover patch.

It is possible to use a tackifier as component of the reservoir layer which has the effect that this is a pressure-sensitive adhesive layer. Examples of suitable tackifiers are abietyl alcohol and its derivatives, e.g. abietyl esters.

The polymeric carrier material of the reservoir layer may additionally be of such a nature that this is a "pressure-sensitive adhesive" layer. In this case, monomers which, as constituent of the polymeric carrier material, contribute to the presence of pressure-sensitive adhesive properties are used for producing the polymeric carrier material. Suitable monomers are: polysiloxanes, polyisobutylenes and polyacrylates, preferably those composed of acrylic acid and/or methylacrylic acid and/or their esters, e.g. isooctyl acrylate, 2-ethylhexyl acrylate etc. The property of being pressure-sensitive adhesive refers to a material in the dry form and at room temperature having a permanent initial tack which makes the material able to adhere firmly to a large number of different materials without the pressure required for this being more than can be exerted with a finger.

In a further embodiment it is possible to use an additional pressure-sensitive adhesive layer which is provided with a higher content of tackifiers. In a further embodiment it is possible to use a cover patch. In this case, the reservoir layer comprising the at least one active pharmaceutical ingredient is covered with a composite of backing layer and pressure-sensitive layer to an extent which results in a projecting rim. The pressure-sensitive adhesive layer of the projecting rim is able to ensure continuous contact between surface of the skin and reservoir layer.

The achievement of the invention is the method by which this at least one active pharmaceutical ingredient is administered to the user to a user (patient) requiring continuous administration of this active pharmaceutical ingredient over a prolonged period. The method includes the steps of a) attachment of a transdermal therapeutic system comprising a backing layer, a reservoir layer comprising the at least one active pharmaceutical ingredient, and an adhesive to the particular site on the surface of this person's skin, b) maintenance of the contact between the active ingredient-releasing side of the transdermal therapeutic system and the particular site on the surface of the skin over a prolonged period and c) removal of the transdermal therapeutic system after its intended period of use has elapsed, where the prolonged period includes at least one time segment associated with intensive exposure to water of the TTS adhering on the surface of the skin.

The following examples serve to illustrate the method of the invention.

1. Comparative Example With a TTS Known From the Prior Art.

A TTS produced as in example 1 of DE 38 43 239 and intended to be worn by a patient over a prolonged period of 72 hours is stuck onto the skin of a test subject. A wearing time of 24 hours is followed by the test subject taking a vigorous shower over a period of 5 minutes, during which the TTS adhering to the skin is exposed to the shower water. It is observed that the TTS detaches from the skin during this showering process. Continuous delivery of the active ingredient over the intended prolonged period is thus no longer possible.

2. Example With a TTS of the Invention

A TTS comprising a backing layer composed of a PET fabric and of a pressure-sensitive adhesive reservoir layer with a content of 10% by weight of the active pharmaceutical ingredient buprenorphine is stuck onto the skin of a further test subject. This TTS is to be worn over a prolonged period of 72 hours. During this period, the test subject takes three baths each lasting 10 minutes, during which the TTS adhering to the skin is exposed to the bath water. Detachment from the skin is not observed during these baths. The active ingredient is thus delivered continuously to the skin also during the prolonged period of 72 hours.

3. Comparative Example With a Further TTS of the Invention

A further TTS comprising a backing layer composed of a PET fabric and of a pressure-sensitive adhesive reservoir layer with a content of 10% by weight of the active pharmaceutical ingredient buprenorphine is stuck onto the skin of a further test subject. The TTS is to be worn over a prolonged period of 168 hours. During this period, the test subject takes four showers each over a period of 5 minutes and takes three baths each lasting 10 minutes. The TTS adhering to the skin is exposed to the water during these shower processes and baths. Detachment of the TTS is not observed.

It is thus shown that the design of the transdermal therapeutic system (TTS) of the invention enables the active ingredient to be delivered continuously over a prolonged period to the skin, even if at least one time segment associated with intensive exposure to water of the TTS adhering to the skin occurs during this period.

The transdermal therapeutic system for administering at least one active pharmaceutical ingredient through the skin of a person requiring the continuous administration of this active ingredient over a prolonged period, where this prolonged period includes at least one time segment of intensive exposure to water of the transdermal therapeutic system, comprises a backing layer, a reservoir layer and an adhesive and has the innovation that the adhesive retains its adhesive properties over said prolonged period.

The figures show three different embodiment of designs of transdermal therapeutic systems (TTS) which comprise the design elements mentioned in the description. The reference numbers therein have the following meaning:

1=backing layer
2=reservoir layer
3=control membrane
4=pressure-sensitive adhesive layer
5=support film Modifications of the embodiments described herein will be apparent to the person skilled in the art of the transdermal administration of active ingredients and are intended to be within the scope of the claims.

The invention claimed is:

1. A transdermal therapeutic system (TTS) comprising:
   a backing layer; and
   a reservoir layer comprising:
      (−)-5,6,7,8,-tetrahydro-6-[propyl[2-(2-thienyl)ethyl]amino]-1-naphthol as active pharmaceutical ingredient; and
      at least one polymeric carrier material selected from the group consisting of water-repelling polymers, water swellable polymers, water-soluble polymers and water-vapor permeable polymers;
   wherein the TTS is configured to adhere continuously to the surface of a user's skin over a prolonged period; and
   wherein the active pharmaceutical ingredient (−)-5,6,7,8,-tetrahydro-6-[propyl[2-(2-thienyl)ethyl]amino]-1-naphthol is delivered transdermally during the prolonged period.

2. The transdermal therapeutic system as claimed in claim 1;
   wherein the reservoir layer further comprises:
      a polymeric carrier material made of at least one water-repelling polymer.

3. The transdermal therapeutic system as claimed in claim 1;
wherein the prolonged period is between at least 24 hours and of up to 168 hours.

4. The transdermal therapeutic system as claimed in claim 1;
wherein the at least one polymeric carrier material which comprises at least one compound selected from the group consisting of polysiloxanes, polyisobutylenes, and polyacrylates.

5. The transdermal therapeutic system as claimed in claim 4;
wherein the reservoir layer further comprises a tackifier.

6. The transdermal therapeutic system as claimed in claim 1;
wherein the content of the active pharmaceutical ingredient (−)-5,6,7,8,-tetrahydro-6-[propyl[2-(2-thienyl)ethyl]amino]-1-naphthol in the reservoir layer is sufficient to deliver the active pharmaceutical ingredient continuously to the surface of the user's skin during the prolonged period of between at least 24 hours and of up to 168hours; and
wherein the adhesion of the TTS is not interrupted during the at least one time segment of intensive exposure to water of the TTS adhering to the surface of the user' skin.

7. A transdermal therapeutic system (TTS) comprising:
a backing layer;
a reservoir layer comprising:
(−)-5,6,7,8,-tetrahydro-6-[propyl[2-(2-thienyl) ethyl] amino]-1-naphthol as active pharmaceutical ingredient; and
an adhesive layer, comprising an adhesive, which confers pressure-sensitive adhesive properties onto the TTS;
wherein the adhesive layer is configured to adhere continuously to the surface of a user's skin over a prolonged period; and
wherein the active pharmaceutical ingredient (−)-5,6,7,8,-tetrahydro-6-[propyl[2-(2-thienyl)ethyl]amino]-1-naphthol is delivered transdermally during the prolonged period.

8. The transdermal therapeutic system as claimed in claim 7, further comprising:
a membrane layer which controls the rate of release of the active pharmaceutical ingredient.

9. The transdermal therapeutic system as claimed in claim 7;
wherein the reservoir layer further comprises:
a polymeric carrier material made of at least one water-repelling polymer.

10. The transdermal therapeutic system as claimed in claim 7;
wherein the prolonged period is between at least 24 hours and of up to 168 hours.

11. The transdermal therapeutic system as claimed in claim 7;
wherein the adhesive comprises at least one compound selected from the group consisting of polysiloxanes, polyisobutylenes, and polyacrylates.

12. The transdermal therapeutic system as claimed in claim 7;
wherein the adhesive comprises a tackifier.

13. The transdermal therapeutic system as claimed in claim 7;
wherein the content of the active pharmaceutical ingredient (−)-5,6,7,8,-tetrahydro-6-[propyl[2-(2-thienyl) ethyl]amino]-1-naphthol in the reservoir layer is sufficient to deliver the active pharmaceutical ingredient continuously to the surface of the user's skin during the prolonged period of between at least 24 hours and of up to 168hours; and
wherein the adhesion of the ITS is not interrupted during the at least one time segment of intensive exposure to water of the TTS adhering to the surface of the user' skin.

14. A method for transdermally administering (−)-5,6,7,8,-tetrahydro-6-[propyl[2-(2-thienyl)ethyl]amino]-1-naphthol to a user requiring continuous administration of (−)-5,6,7,8,-tetrahydro-6-[propyl[2-(2-thienyl)ethyl]amino]-1-naphthol over a prolonged period of between at least 24 hours and of up to 168 hours, comprising:
a) attaching a transdermal therapeutic system (TTS) to a particular site on a surface of the user's skin, the transdermal therapeutic system comprising:
a backing layer; and
a reservoir layer comprising:
(−)-5,6,7,8,-tetrahydro-6-[propyl[2-(2-thienyl)ethyl] amino]-1-naphthol; and
at least one polymeric carrier material selected from the group consisting of water-repelling polymers, water swellable polymers, water-soluble polymers and water-vapor permeable polymers;
b) maintaining contact between an active ingredient-releasing side of the transdermal therapeutic system and the particular site on the surface of the user's skin over an intended prolonged period; and
c) removing the transdermal therapeutic system after its intended prolonged period of use has elapsed.

15. The method as claimed in claim 14;
wherein the prolonged period comprises between at least 24 hours and of up to 168 hours.

16. A method for transdermally administering (−)-5,6,7,8,-tetrahydro-6-[propyl[2-(2-thienyl)ethyl]amino]-1-naphthol to a user requiring continuous administration of (−)-5,6,7,8,-tetrahydro-6-[propy[2-(2-thienyl)ethyl]amino]-1-naphthol over a prolonged period of between at least 24 hours and of up to 168 hours, comprising:
a) attaching a transdermal therapeutic system (TTS) to a particular site on a surface of the user's skin, the transdermal therapeutic system comprising:
a backing layer;
a reservoir layer comprising:
(−)-5,6,7,8,-tetrahydro-6-[propyl[2-(2-thienyl)ethyl] amino]-1-naphthol; and
an adhesive layer, comprising an adhesive, which confers pressure-sensitive adhesive properties onto the TTS;
b) maintaining contact between an active ingredient-releasing side of the transdermal therapeutic system and the particular site on the surface of the user's skin over an intended prolonged period; and
c) removing the transdermal therapeutic system after its intended prolonged period of use has elapsed.

17. The method as claimed in claim 16;
wherein the prolonged period comprises between at least 24 hours and of up to 168 hours.

18. The transdermal therapeutic system as claimed in claim 1;
wherein at least one time segment associated with intensive exposure to water of the TTS adhering to the surface of the skin occurs during the prolonged period.

19. The transdermal therapeutic system as claimed in claim 18;

wherein the intensive exposure to water is selected from the group consisting of washing, bathing, showering, and visiting a sauna.

20. The transdermal therapeutic system as claimed in claim 7;
wherein at least one time segment associated with intensive exposure to water of the TTS adhering to the surface of the skin occurs during the prolonged period.

21. The transdermal therapeutic system as claimed in claim 20;
wherein the intensive exposure to water is selected from the group consisting of washing, bathing, showering, and visiting a sauna.

22. The method as claimed in claim 14;
wherein the prolonged period includes at least one time segment associated with intensive exposure to water of the TTS adhering to the surface of the skin.

23. The method as claimed in claim 22;
wherein the intensive exposure to water is selected from the group consisting of washing, bathing, showering, and visiting a sauna.

24. The method as claimed in claim 16;
wherein the prolonged period includes at least one time segment associated with intensive exposure to water of the TTS adhering to the surface of the skin.

25. The method as claimed in claim 24;
wherein the intensive exposure to water is selected from the group consisting of washing, bathing, showering, and visiting a sauna.

26. The transdermal therapeutic system as claimed in claim 1;
wherein the content of the active pharmaceutical ingredient in the reservoir layer is from 0.5 to 45% by weight.

27. The transdermal therapeutic system as claimed in claim 1;
wherein the content of the active pharmaceutical ingredient in the reservoir layer is from 3 to 25% by weight.

28. The transdermal therapeutic system as claimed in claim 7;
wherein the content of the active pharmaceutical ingredient in the reservoir layer is from 0.5 to 45% by weight.

29. The transdermal therapeutic system as claimed in claim 7;
wherein the content of the active pharmaceutical ingredient in the reservoir layer is from 3 to 25% by weight.

30. The transdermal therapeutic system as claimed in claim 1;
wherein the backing layer is a film web with a thickness of from 2 to 50μm.

31. The transdermal therapeutic system as claimed in claim 7;
wherein the backing layer is a film web with a thickness of from 2 to 50μm.

32. A transdermal therapeutic system (TTS) comprising:
a backing layer; and
a reservoir layer comprising:
(−)-5,6,7,8,-tetrahydro-6-[propyl[2-(2-thienyl)ethyl]amino]-1-naphthol as active pharmaceutical ingredient in an amount of from 3 to 25% by weight; and
at least one polymeric carrier material comprising polyisobutylene;
wherein the TTS is configured to adhere continuously to the surface of a user's skin over a prolonged period; and
wherein the active pharmaceutical ingredient (−)-5,6,7,8,-tetrahydro-6-[propyl[2-(2-thienyl)ethyl]amino]-1-naphthol is delivered transdermally during the prolonged period.

* * * * *